United States Patent
Howe (10) Patent No.: US 9,610,145 B2
(45) Date of Patent: Apr. 4, 2017

(54) PRECISION-MILLED DENTURE TEETH AND METHOD AND DEVICES FOR MAKING SAME

(71) Applicant: CMP INDUSTRIES LLC, Albany, NY (US)

(72) Inventor: Devon O. Howe, Saratoga Springs, NY (US)

(73) Assignee: CMP Industries LLC, Albany, NY (US)

(*) Notice: Subject to any disclaimer, the term of this patent is extended or adjusted under 35 U.S.C. 154(b) by 475 days.

(21) Appl. No.: 14/212,532

(22) Filed: Mar. 14, 2014

(65) Prior Publication Data

US 2014/0272777 A1 Sep. 18, 2014

Related U.S. Application Data

(60) Provisional application No. 61/798,778, filed on Mar. 15, 2013.

(51) Int. Cl.
| | | |
|---|---|---|
| *A61C 13/08* | (2006.01) | |
| *A61C 13/00* | (2006.01) | |
| *A61C 13/12* | (2006.01) | |
| *A61C 9/00* | (2006.01) | |

(52) U.S. Cl.
CPC ...... *A61C 13/0004* (2013.01); *A61C 13/0006* (2013.01); *A61C 13/081* (2013.01); *A61C 13/12* (2013.01); *A61C 9/004* (2013.01); *A61C 13/0022* (2013.01)

(58) Field of Classification Search
CPC ............ A61C 13/0004; A61C 13/0006; A61C 13/081; A61C 13/12; A61C 13/0022; A61C 9/004

USPC ...... 264/16, 17, 19, 20, 138; 433/213, 202.1
See application file for complete search history.

(56) References Cited

U.S. PATENT DOCUMENTS

| | | | | |
|---|---|---|---|---|
| 4,970,032 | A  * | 11/1990 | Rotsaert ............ | A61C 13/0003 264/139 |
| 5,788,498 | A  * | 8/1998 | Wohlwend ......... | A61C 13/0003 264/19 |
| 6,488,503 | B1 * | 12/2002 | Lichkus ............... | A61C 13/087 264/19 |
| 6,669,875 | B2 * | 12/2003 | Meyertholen ...... | A61C 13/0003 264/138 |
| 7,103,830 | B1 * | 9/2006 | Dong .................... | H03M 5/145 714/781 |
| 8,641,938 | B2 | 2/2014 | Howe | |
| 9,345,561 | B2 * | 5/2016 | Johnson ............. | A61C 13/0022 |
| 2003/0073394 | A1 * | 4/2003 | Reidt ................. | A61C 13/0022 451/398 |

(Continued)

*Primary Examiner* — Nahida Sultana
(74) *Attorney, Agent, or Firm* — John M. Hammond; Patent Innovations LLC (57) ABSTRACT

A device for making artificial teeth for a denture. The device is comprised of a nest comprised of a lower portion formed of a rigid material and having an upper planar surface, and an upper portion contiguous with the upper planar surface of the lower portion, and formed of an elastomeric material and configured to receive a plurality of the artificial teeth and hold the teeth in predetermined positions relative to the upper planar surface. A method for making artificial teeth using the nest and a fixative applied thereto is also disclosed. The method may include milling of the artificial teeth by a CAD-CAM operated mill.

11 Claims, 7 Drawing Sheets

(56) References Cited

U.S. PATENT DOCUMENTS

| | | | |
|---|---|---|---|
| 2003/0138756 A1* | 7/2003 | Monkmeyer | A61O 5/10 433/202.1 |
| 2012/0009541 A1* | 1/2012 | Holzner | A61C 13/0027 433/49 |
| 2012/0171635 A1* | 7/2012 | Karlsson | A61C 5/002 433/50 |
| 2012/0183921 A1* | 7/2012 | Karlsson | A61C 5/002 433/49 |
| 2014/0295371 A1* | 10/2014 | Huffman | A61C 11/00 433/49 |

* cited by examiner

PRECISION-MILLED DENTURE TEETH AND METHOD AND DEVICES FOR MAKING SAME

CROSS-REFERENCE TO RELATED PATENT APPLICATIONS

This application claims priority from U.S. provisional patent Application No. 61/798,778 filed Mar. 15, 2013, the disclosure of which is incorporated herein by reference.

BACKGROUND

Technical Field

Dental prostheses and apparatus and methods of manufacturing them. In particular, methods of making artificial denture teeth, devices for making artificial denture teeth, and dental prostheses which include artificial denture teeth made by the devices and method. The methods for making the artificial denture teeth may be implemented by a computer-controlled machine.

Description of Related Art

Heretofore, the manufacturing of dental prostheses has been a highly labor intensive process requiring multiple fittings to a patient in need of them, and many steps that must be performed at the hands of skilled artisans. The dental prosthesis may be a complete upper and/or lower set of prosthetic teeth and their mountings, such as a denture or partial denture. The prosthesis may be a dental crown, which is a rigid fitting that completely encloses or caps a tooth. The prosthesis may be a dental bridge, which is an artificial tooth or teeth that replaces missing natural teeth and that is joined to adjacent remaining teeth.

By way of illustration of the degree of labor that is required to make a dental prosthesis according to certain methods, the following are the steps currently practiced in many "dental laboratories" for the fabrication of a conventional fixed crown dental prosthetic:

1) A dentist prepares the patient's tooth (or teeth) to be fitted with the crown by removing tooth structure that is decayed, or to provide space that will be occupied by the crown.

2) An accurate impression of the patient's existing gums and prepared teeth, including the tooth or teeth that will receive the crown, is made by the dentist at the dentist's office. The impression may be made using a silicone elastomer such as polyvinyl siloxane.

3) The impression is removed from the patient's mouth and gypsum material is poured into the impression. The gypsum hardens and forms a model (replica) of the dentition to be treated.

4) Wax is typically used to make a coping, i.e., a thin metal substructure on the surface of the model using the "lost wax technique." The gypsum model is covered by a thin layer of wax, which is then covered by a phosphate "investment" material. The gypsum model with wax and investment layers is heated to melt of burn out the wax, thereby leaving a void in its place.

5) Metal is cast into the void created by the loss of wax to create the metal coping.

6) The metal coping is finished with grinding stones and typically heat-treated.

7) Porcelain powder dispersed in water is painted onto the metal coping.

8) The porcelain is fired in a furnace to sinter it into a continuous hard coating on the metal coping, resulting in the finished crown.

It can be seen that the above process is highly labor-intensive. Each of the steps introduces a potential for a processing error. Even the slightest error, such as the investment being too cool, or the powder/water ratio of the investment being incorrect, may cause the crown to fit too tightly in the patient's mouth, resulting in improper occlusion (upper and lower teeth engagement). The crown may thus have to be scrapped or reworked through at least one iteration of additional process steps at considerable cost to the patient, dentist, and/or manufacturing lab.

Currently, Computer Aided Design and Computer Aided Manufacturing (CAD/CAM) for "fixed" restorative dentistry has evolved to the point where a digital impression of a patient's dentition can now be made in the dentist's office and the entire process can be computer implemented. However, certain shortcomings still remain in fixed restorative dentistry as presently practiced. For example, subtle irregularities often found in anterior (front) teeth are difficult to replicate using CAD/CAM processes. Manual methods of making anterior fixed prosthetics enable unlimited aesthetic options, only limited by the creativity of the artisan, a dental laboratory technician. Some CAD/CAM techniques involve the use of milling a monolithic block of ceramic that does not deliver optimal esthetics, especially for anterior applications. For example, rather than being a monotone opaque white, most natural teeth exhibit translucency and subtle color variations. A common solution for this problem is for a dental technician to apply a stain and/or glaze of porcelain over the prosthetic made by CAD/CAM. However, this manual step may negate a primary benefit of CAD/CAM, which is precise dimensional accuracy.

With regard to the manufacturing of removable dental prosthetics, such as dentures and partial dentures, implementation of CAD/CAM has begun to occur. A key technology that is used in CAD/CAM denture manufacturing is "fused deposition modeling" (FDM). In FDM, a computer-controlled machine builds a three dimensional part by ejecting microscopic droplets of material while repeatedly traversing in an x-y plane, building the part layer-by layer. In a sense, the machine "ink-jet prints" each layer, and hence FDM is also referred to as "3D printing." The physical model is built according to a three-dimensional virtual model that is prepared using CAD software and uploaded to the FDM machine.

CAD/CAM systems have recently been developed and used for the fabrication of partial denture frameworks. One such system uses a "haptic" device, which mimics a waxing tool that is familiar to dental technicians. However, this system generates only a CAD replica in plastic (made by a 3D printer), which requires subsequent extensive processing to obtain a metal partial denture framework. Hence there are still many error-prone steps after the CAD replica is made that can result in a poorly-fitting partial denture framework.

There have been some efforts by major manufacturers of dental materials to make a system to produce a complete (full) denture by 3D printing. The system includes a 3-dimensional scanner for scanning an impression, software for creating a 3-dimensional model of the denture, and the fused deposition modeling equipment for "printing" the denture. However, the materials available to use in 3-dimensional printers are neither as dense nor cross-linked like a normal plastic artificial tooth. Hence a problem remains with the resulting dentures because the denture teeth that are made with available 3D printing plastic materials are not sufficiently wear-resistant.

An alternative approach to denture fabrication is to first make a denture base using a milling machine, which may be computer controlled. Sockets are then milled by the machine into the denture base, and pre-fabricated artificial teeth are placed into the sockets. A problem with this approach is that most of the teeth must be adjusted to some extent to fit within the space required in order for the denture to properly occlude (fit together) with the opposing arch of the opposing denture or the patients existing opposing teeth. Manual labor is required for the adjustment of teeth; therefore, the potential for errors is introduced into the manufacturing process.

Another problem with this method is that artificial teeth are not consistently sized. They are made from a molding process, with the molds being used for many years. Over the course of use, material from the wall of the mold will wear away, resulting in a mold cavity increasing in size. Hence a tooth made from a mold that has been in service for ten years will be larger than a tooth made when the mold was new. Additionally, molds contain multiple cavities, and the wear is not necessarily uniform. Thus the combination of wear with time and non-uniform wear results in the production of teeth that vary dimensionally within any given tooth size. Moreover, in the denture fabrication marketplace, artificial teeth are returnable for credit. It therefore becomes highly probable that artificial teeth produced 20 years ago from a new mold are in circulation with teeth produced very recently from the same but aged mold having different dimensions.

There is thus a problem in that the dimensional variation of artificial teeth is significant with respect to the dimensions of the sockets formed by the milling machine in which the teeth are to be fitted. The sockets must be milled sufficiently large so as to receive the largest tooth encountered within a given tooth size and shape (i.e. incisor, canine, molar, etc.), and countermeasures taken when the tooth is too small and does not fight tightly into its socket. One countermeasure is to use an acrylic repair resin to secure the teeth into position and to fill the gap(s), of various sizes that may be present around an undersized tooth. However, this practice is undesirable. Additional labor is required for this step, which is costly and which is likely to be a manual process that can introduce potential errors to the denture fabrication.

In the conventional approach, a dental technician often adjusts each artificial tooth in a way to optimize retention. For example, a dental technician will remove the "glaze" from a denture tooth (shiny and hard surface of the tooth created from a metal mold) to form a better bond with the denture base. Also, "diatoric" holes are often cut into the bottom or side of the tooth, or both, to allow denture base acrylic material to flow in an optimal path to increase the surface area and create mechanical retention in a tooth.

Artificial teeth that have an aesthetically pleasing appearance are generally made of highly cross-linked polymethylmethacrylate plastic, but also may be made of porcelain. Such artificial teeth are made with a series of metal dies in which the teeth are formed one-layer at a time. When all of the layers are completed, the "green" tooth is then heated to polymerize the plastic (or super-heated in the case of porcelain teeth). The heating process completes the cross-linking process in plastic teeth to make the teeth resistant to wear from the forces of mastication.

The Applicant's commonly owned U.S. Pat. No. 8,641,938, the disclosure of which is incorporated herein by reference, discloses a method of milling a denture out of a disc of denture base material and filling voids milled in the disc with tooth-colored resin. Although this is an effective method, the total time needed for the various milling steps may be longer than desired in some instances, thus leaving an opportunity for further improvement in cost and throughput of denture fabrication.

In summary, there remains a need for a method and apparatus to adjust pre-manufactured artificial teeth in a consistent and low-cost manner so that they fit properly in corresponding space in a denture base that are intended to receive them. There is also a need for the adjusting method to also optimize tooth retention in the denture base.

SUMMARY

In accordance with the present disclosure, the problem of adjusting pre-manufactured denture teeth to precise desired dimensions in a manner that requires minimal manual labor is solved by placing pre-manufactured teeth into a "nest" and then affixing them into a consistent position, so that CAD-CAM software can instruct a milling system to mill the teeth such that they fit the corresponding sockets and space elements milled in a denture base. The nest is specific to a certain mold of manufactured artificial denture teeth and is made with an elastomeric material to allow for slight differences in the geometries of teeth produced using a given mold. In addition, the CAD-CAM software can place additional retentive features in the teeth (such as "diatorics") so that the risk of de-bonding from the denture base is minimized.

In practicing a method of the present disclosure, the set of "nested" teeth are placed into a milling machine, which mills the surfaces of the artificial teeth that are closest to the patient's ridge in order to break the shiny surfaces of the teeth, thereby facilitating bonding with the denture base. In addition, the mill may reduce the size of the vertical dimension of each tooth in order to fit the required space in the patient's mouth. This may be programmed in the CAD-CAM software that operates the mill. Lastly, the mill may create retentive features, such as a concave shape in the tooth ridge-lap area to fit a corresponding convex shape milled in the denture base.

More specifically, in accordance with the present disclosure, there is provided a device for making artificial teeth for use in a dental prosthesis such as a denture. The device is comprised of a nest comprising a lower portion and an upper portion. The lower portion is formed of a rigid material and has an upper planar surface. The upper portion is contiguous with the upper planar surface of the lower portion, and is formed of an elastomeric material and configured to receive a plurality of the artificial teeth and hold the teeth in predetermined positions relative to the upper planar surface of the lower portion. The elastomeric material is configured to place a distal edge of each of the plurality of artificial teeth in contact with the upper planar surface of the lower portion of the nest. The predetermined positions may be defined to enable milling of each of the plurality of teeth by a CAD-CAM milling system.

The device may be further comprised of a fixative contiguous with an upper surface of the elastomeric material. The fixative may be made of a flowable material applied to the elastomeric material that subsequently forms a rigid material. The fixative material may be an adhesive material or a wax material. The fixative maintains the teeth in the predetermined positions for subsequent milling of the teeth to desired dimensions.

In another aspect of the present disclosure, there is provided a method for making artificial teeth for use in a dental prosthesis, such as a denture. The method comprises inserting a plurality of artificial teeth into an elastomeric material of a nest, and contacting respective distal edges of each of the teeth with an upper planar surface of a rigid bottom of the nest that is contiguous with the elastomeric material of the nest; forming a rigid fixative contiguous with the elastomeric material of the nest, thereby embedding a central region of each of the plurality of teeth in the rigid fixative and rendering each of the plurality of teeth in a fixed position; separating the nest from the rigid fixative and from the plurality of teeth; securing the rigid fixative with the plurality of teeth in fixed positions on a milling machine; and milling each of the plurality of teeth to desired dimensions. The forming of the rigid fixative may be performed by applying a flowable material to the elastomeric material, the flowable material subsequently forming the rigid fixative.

The method may further comprise scanning the rigid fixative with the plurality of teeth in fixed positions to obtain three-dimensional data on each of the plurality of teeth prior to milling each of the plurality of teeth to desired dimensions. The three-dimensional data of each of the plurality of teeth may be used by a computer controlling the milling each of the plurality of teeth to desired dimensions.

The fixed positions may be predefined by using a computer aided design software program. The milling of each of the plurality of teeth to desired dimensions may be performed by a milling machine controlled by a computer according to a CAD-CAM program.

The ridge-lap surfaces of the plurality of teeth may be milled to desired dimensions, and may include retentive features for engagement with denture base material. The distal edges of the plurality of teeth are milled to desired dimensions in order to provide desired vertical dimensions of the plurality of teeth and/or to provide improved occlusion of the teeth.

BRIEF DESCRIPTION OF THE DRAWINGS

The present disclosure will be provided with reference to the following drawings, in which like numerals refer to like elements, and in which.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. In the following disclosure, certain components may be identified with adjectives such as "top," "upper," "bottom," "lower," "left," "right," etc. These adjectives are provided in the context of the orientation of the drawings, which is arbitrary. The description is not to be construed as limiting the methods and apparatus disclosed herein to use in a particular spatial orientation. The instant methods and apparatus may be used in orientations other than those shown and described herein.

As used herein, the term or acronym "CAD-CAM" refers to Computer Aided Design and Computer Aided Manufacturing. Depending upon the context of use, the term may be referring to a computer software program for the design of an article such as a tooth or denture, or a computer software program for the manufacture of an article such as a tooth or denture; or a combination of both. The term may also be used with reference to a machine, which is used to manufacture an article such as a tooth or denture, and which is controlled by a computer that executes such computer software program(s).

Figure 1:
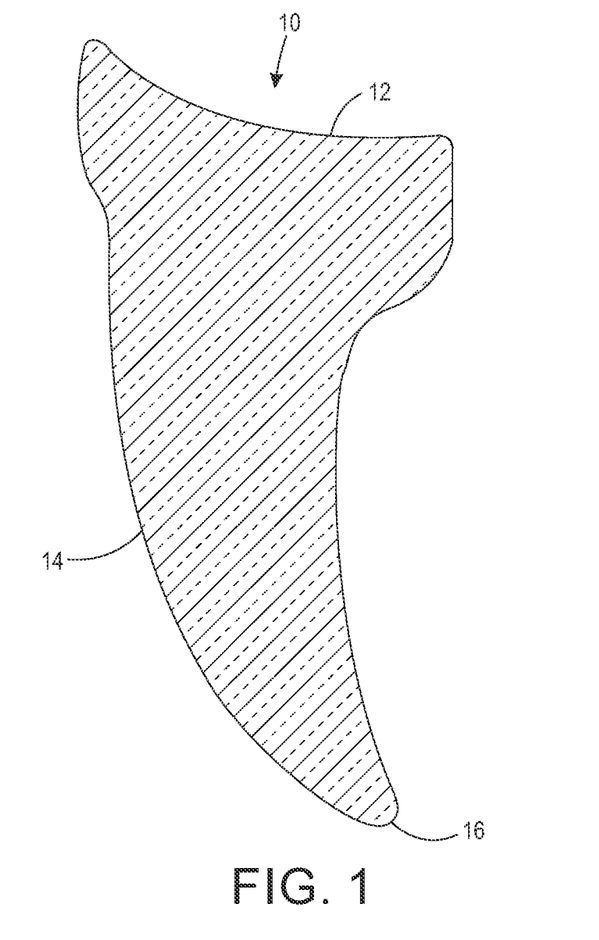
FIG. 1 is a side cross-sectional view of a central incisor tooth that depicts the ridge-lap, labial surface, and incisal surface of the tooth.

Turning first to FIG. 1, the basic anatomy of a central incisor tooth is depicted. The central incisor tooth is an anterior or "front" tooth, i.e. a tooth that is in the front region of a maxillae or mandible, and that may be in contact with the lips. It is to be understood that the methods and apparatus of the present disclosure are applicable to posterior teeth, such as molar teeth, as well.

The tooth 10 has a ridge-lap surface 12, a labial surface 14, and an incisal edge 16. The incisal edge 16 is the biting or cutting edge, and the labial surface 14 of the tooth 10 is an anterior surface of the tooth that is in contact with the lips (where the tooth is a human tooth). The ridge-lap surface 12 is the surface of the tooth that is beneath the gums and proximate to the root (not shown) of the tooth. In practicing a method of milling teeth according to the present invention, the tooth 10 may be an artificial tooth made of synthetic tooth material, in which case the portion of the tooth that is proximate to the ridge-lap surface 12 may be embedded in denture base material of a denture (not shown).

In milling an incisor tooth according to the present disclosure, the portion of the tooth that is proximate to ridge-lap surface 12 may be dimensionally altered by the milling method and apparatus so that the tooth can fit into a space in the denture base material, which may be formed by a CAD-CAM based method and apparatus according to a CAD-CAM software program.

Figure 2:
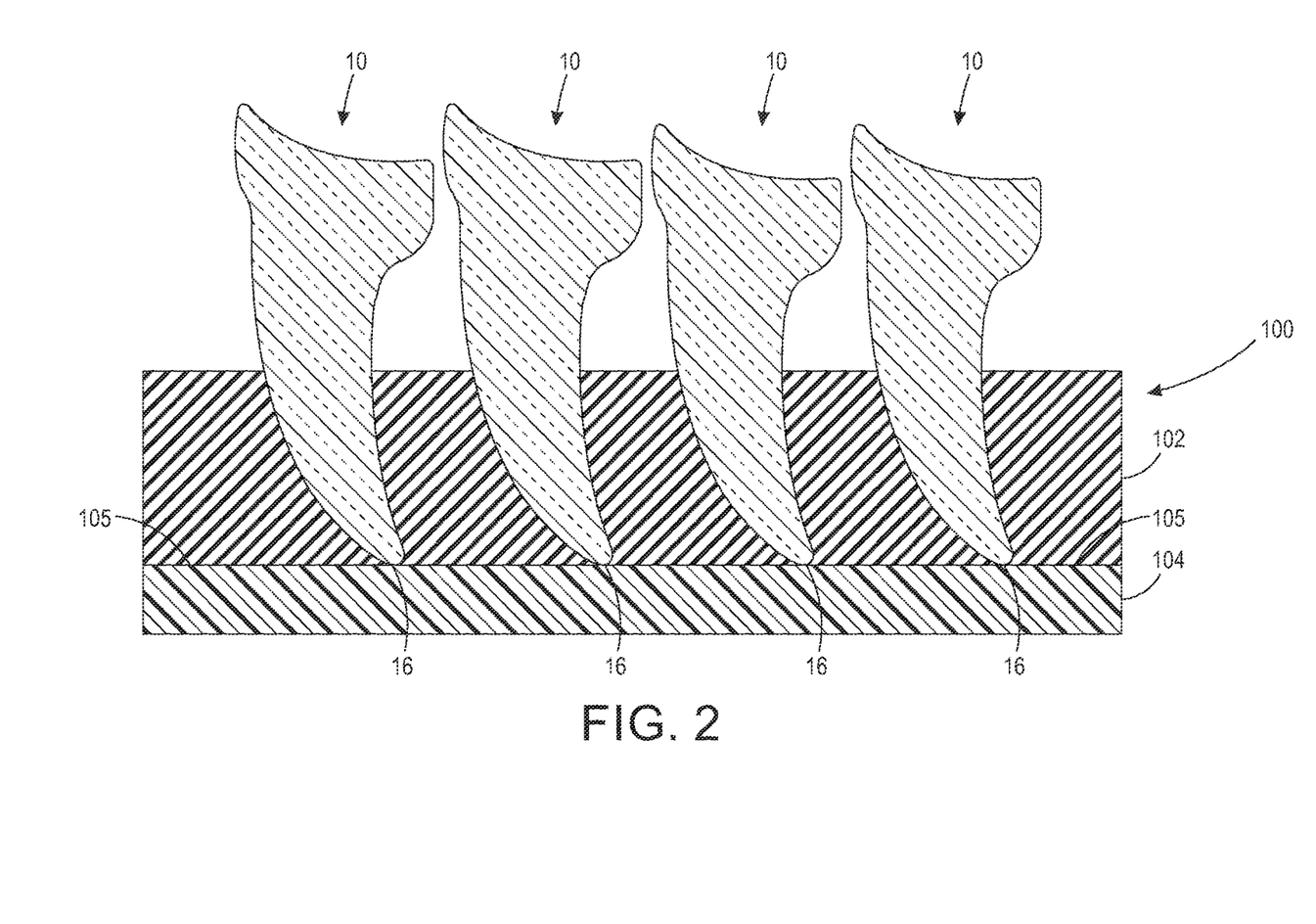
FIG. 2 is a side cross-sectional view of four central incisor teeth of FIG. 1 embedded in a "nest" for indexing the teeth in a predefined position.

FIG. 2 is a side cross-sectional view of four central incisor teeth, such as teeth 10 of FIG. 1 embedded in a "nest." The nest 100 is comprised of an upper portion 102 made of an elastomeric material, and a lower portion 104 made of a rigid material. It will be apparent that the number of teeth 10 embedded in the nest 100 may vary, with the nest 100 being sized accordingly.

In using the nest 100, the teeth 10 are inserted into the elastomeric material 102. The teeth 10 are inserted in the same orientation and height relative to the rigid bottom 104 in the nest 100. In general, a nest of the present disclosure is specific to a certain mold of manufactured artificial denture teeth. In the embodiment depicted in FIGS. 2-9, the nest 100 is specific to a particular mold for making central incisor teeth. The elastomeric material in the upper portion 102 of the nest 100 allows for teeth 10 with slightly differing dimensions to fit in the nest 100, which is designed for the specific tooth mold of the tooth 10 to be inserted into the nest 100.

An advantageous feature of the nest 100 is that all of the teeth 10 are seated with their respective incisal edges 16 touching the upper surface 105 of the rigid bottom 104 of the nest 100 such that they are all located with respect to the same horizontal plane. (For the milling of posterior teeth such as molars, the cusp tips of such teeth are in contact with the upper surface 105 of the rigid bottom 104 of the nest 100. In general, the distal edges of the teeth to be milled are in contact with the upper surface 105 of the rigid bottom 104 of the nest 100.) In that manner, the CAD software used in designing the teeth 10 can be used in instructions in the CAM software that is used by a milling machine to cut each tooth 10 to a certain height as required.

Another advantageous feature of the nest 100 is that the upper portion 102 is of an elastomeric material. If the upper portion 102 of the nest 100 was rigid and not elastomeric, some of the teeth 10 would not fit in the nest 100 because teeth manufactured using the same mold are not always exactly the same size, as explained previously herein. In general, in practicing the methods of the present disclosure, the nest 100 serves to index the teeth 10, i.e., place the teeth 10 in a predefined position so that they may be milled in order to fit a denture base (not shown). The denture base may be made by a CAD-CAM system, and the milling of the teeth 10 may also be performed by a CAD-CAM system as will be explained in further detail herein.

Figure 3:
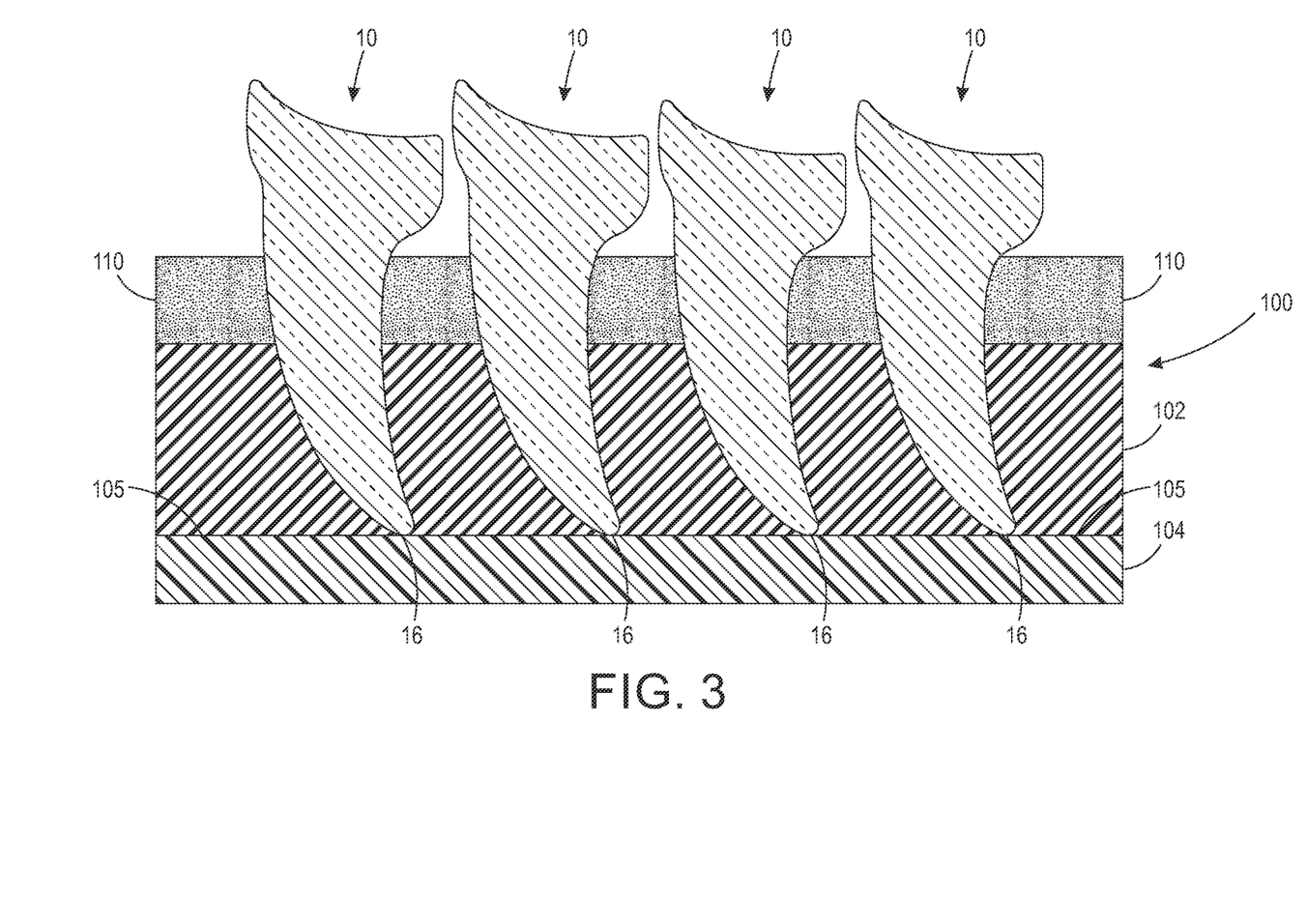
FIG. 3 is a side cross-sectional view of the four central incisor teeth embedded in the nest as shown in FIG. 2, but with a fixative added to stabilize the position of the teeth in the predefined position.

FIG. 3 is a side cross-sectional view of the four central incisor teeth 10 embedded in the nest 100 as shown in FIG. 2, but with a fixative added to stabilize the position of the teeth 10. The fixative 110 may be made of a suitable wax or adhesive material that is a flowable material that subsequently becomes rigid. In certain embodiments, the fixative 110 may be a mixture of waxes such as: paraffin wax (80%) and bees wax (17%) (or Ceresin) and Carnauba Wax (3%). The fixative 110 serves to surround the teeth 10, embedding them in the fixative and maintaining the teeth 10 in the predefined position defined when the teeth 10 were inserted into the nest 100 as described previously. The fixative 110 maintains the teeth 10 in this predefined position during the process of milling the teeth as will be explained subsequently.

Figure 4:
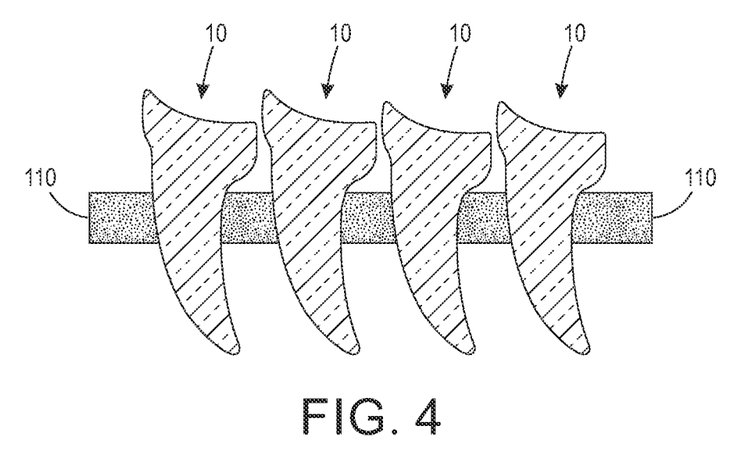
FIG. 4 is a side cross-sectional view of the four central incisor teeth of FIG. 3, but with the nest removed and only the fixative remaining to hold the teeth in the predefined position.

FIG. 4 is a side cross-sectional view of the four central incisor teeth 10 of FIG. 3, but with the nest 100 having been removed, and only the fixative 110 remaining to hold the teeth in the predefined position. The fixative 110, which was initially a flowable material, has become rigid, and can serve as a fixture for subsequent operations.

Figure 5:
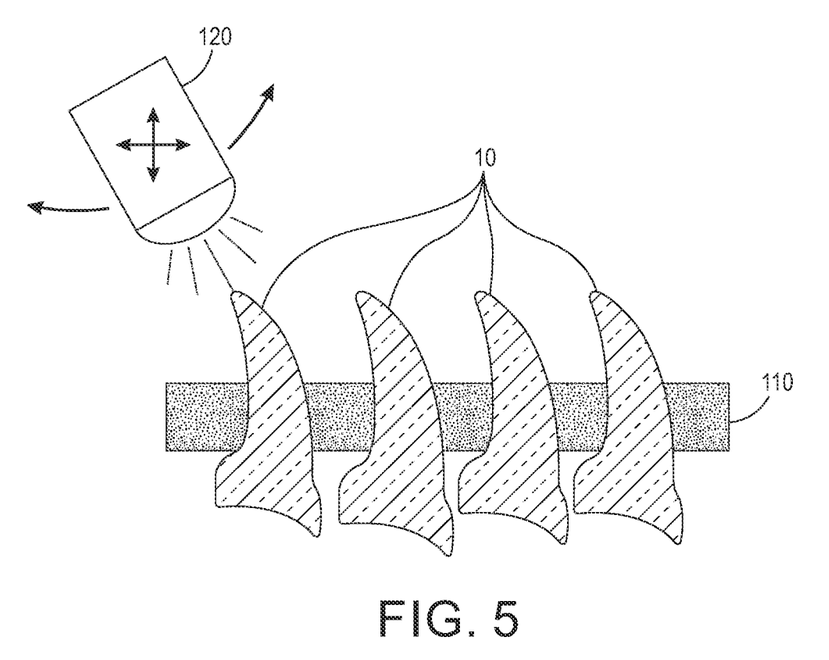
FIG. 5 is a side view of the four central incisor teeth embedded in the fixative material as shown in FIG. 4, and mounted in a scanning system to capture the precise contour of the areas of the teeth exposed outside of the fixative material.

FIG. 5 is a side view of the four central incisor teeth 10 embedded in the fixative 110 as shown in FIG. 4, and mounted in a scanning system to capture the precise contour of the areas of the teeth 10 exposed outside of the fixative 110. The scanning system is comprised of a fixture (not shown) for holding the fixative 110 and teeth 10, and a scanner 120 that is moved by a suitable motion control system (not shown). The motion control system moves the scanner 120 in three dimensions (typically defined via x-y-z orthogonal axes), and is also capable of aiming the scanner 120 along a fourth axis during scanning of the teeth 10. In the embodiment depicted in FIG. 5, the fixative 110 and teeth 10 are shown as having been inverted relative to their positions depicted in FIGS. 3 and 4. The scanner 120 may perform scans with the teeth 10 in the positions of FIGS. 3 and 4, and then perform scans with the teeth 10 in the position of FIG. 5. The scanner 120 may scan the teeth 10 when they are held by the fixture in other positions. Alternatively, the scanning system may be provided with a motion control system that is configured to articulate the scanner 120 through all of the necessary positions while the teeth 10 and fixative 110 are maintained in a fixed position. Alternatively, the scanner 120 may be held stationary, and the teeth 10 and fixative 110 moved relative to the scanner 120.

The scanner 110 captures three-dimensional data or images of the teeth that can be converted to three-dimensional data to provide a three dimensional image or model of the teeth 10 and their position in the fixative 110. The three-dimensional image can then be communicated to a computer (not shown) that controls the operation of a mill during the milling of the teeth 10, as will be described subsequently. By having the additional three-dimensional data on the teeth 10 in the fixative 110, the computer can more precisely mill the teeth 10 in order to fit the vertical and horizontal space provided in a denture base (not shown) that will receive the teeth, as may be defined by the CAD software used in manufacturing the base.

Figure 6:
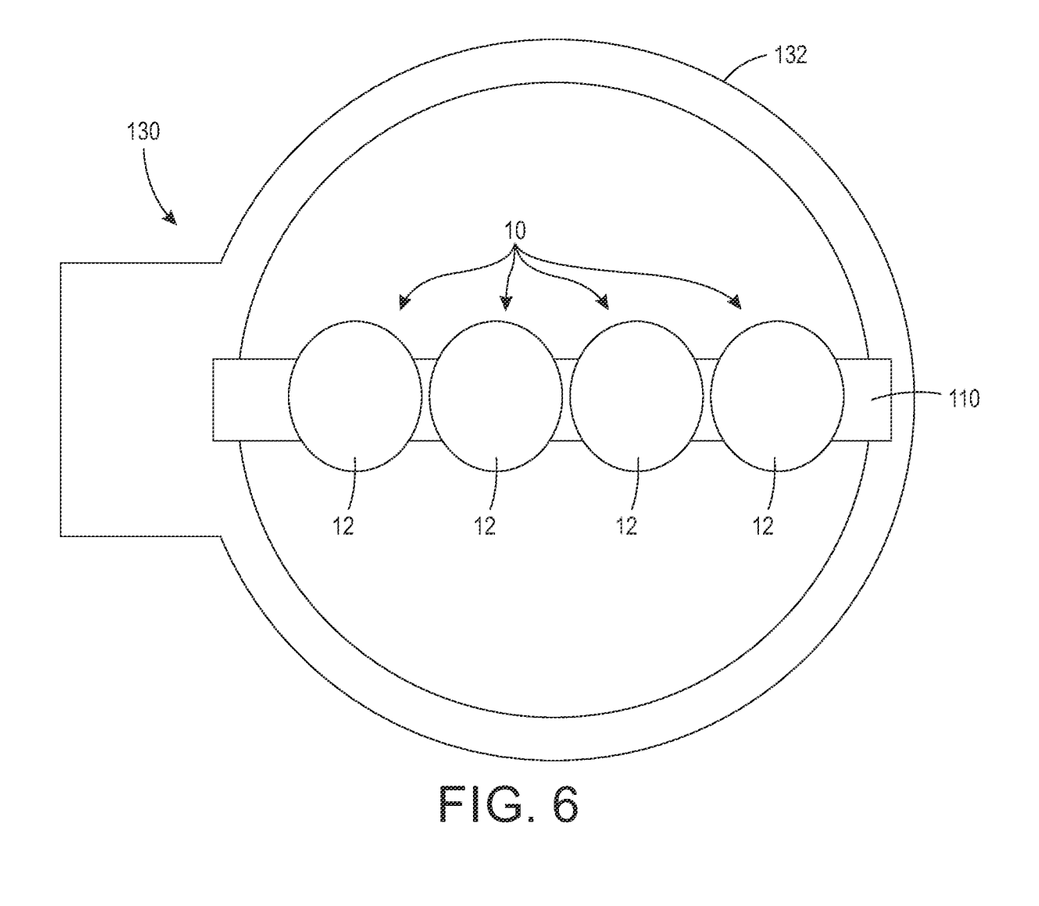
FIG. 6 is a top view of the four central incisor teeth embedded in the fixative as shown in FIG. 4, mounted on a milling machine fixture and ready for certain milling operations on the teeth.
Figure 7:
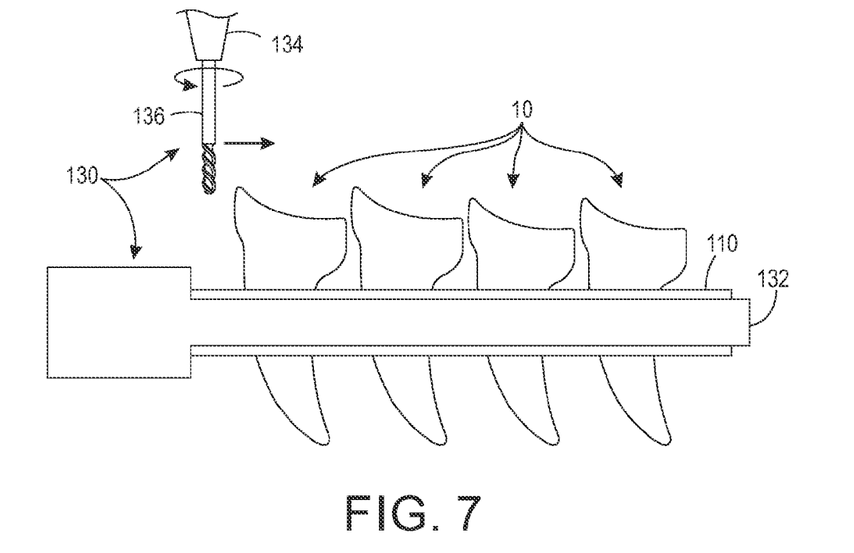
FIG. 7 is a side view of the four central incisor teeth embedded in the fixative as shown in FIG. 4, mounted on the milling machine fixture and ready for certain milling operations on the teeth.

FIG. 6 is a top view of the four central incisor teeth 10 embedded in the fixative 110 as shown in FIG. 4, and mounted on a fixture of a milling machine, and FIG. 7 is a side view of the teeth 10 embedded in the fixative 110, and mounted on the fixture of the milling machine. In FIGS. 6 and 7, the teeth 10 are held by the fixative 110, which in turn is held by the fixture 132 of the milling machine 130. The teeth 10 are held securely and are ready for certain milling operations on the teeth as will be described presently.

For the sake of simplicity of illustration, various details of the milling machine 130, such as a framework, turret, mill bed, motors, and drives are not shown. Such details are well known to those skilled in the art of Computer Numerical Control (CNC) milling machines. Additionally, for the sake of simplicity of illustration, the ridge-lap surfaces 12 of the teeth 10 are shown as simple ellipses in FIG. 6. These surfaces 12 may have shapes other than the ellipses shown.

Referring again to FIG. 7, the milling machine 130 includes a rotating milling tool bit or bur 136 that is removably held by a rotating collet 134. The collet 134 and bur 136 are driven by a rotary motor (not shown) and moved in three dimensional space by a multi-axis x-y-z drive system. Additionally, the collet 134 and tool bit 136 may be articulated along other axes by drives (not shown) that control the axial direction of the bur 136, as is commonly done with multi-axis CNC mills.

Figure 8:
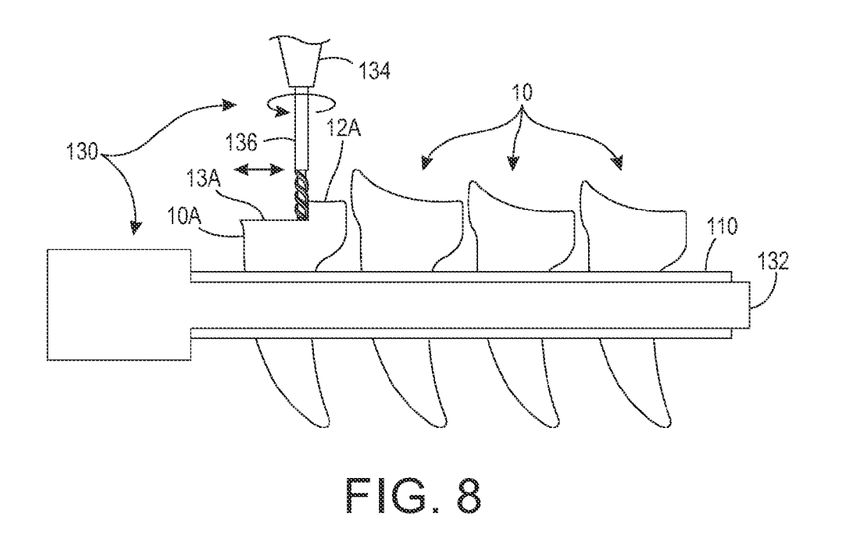
FIG. 8 is a is a side view of the four central incisor teeth and milling machine as shown in FIG. 6, with the tooth milling operation having begun and a milling bur having cut some of the ridge-lap area of a tooth.

Referring to FIG. 8, the milling operation has begun, with the milling bur 136 having cut some of the ridge-lap area 12A of the tooth 10A, thus providing a new ridge-lap surface 13A. By removing the ridge-lap surface 12A of the tooth 10A, the shiny surface of the tooth 10A at that location is removed, leaving a rougher surface that has better adhesion to denture base material. In that manner, bonding with the denture base is facilitated. Additionally, the milling machine 130 removes a specific amount of artificial tooth material from the tooth 10A, and the other teeth 10, as programmed via the CAD-CAM software and executed by the milling machine 130. The amount of material to be removed from the ridge-lap surface 12A (and corresponding ridge lap surfaces 12 of the remaining teeth 10) is predetermined so as to ensure a proper fit of the teeth 10 when they are installed in a denture base (not shown), which may also be made with a CNC milling machine, such as milling machine 130. The dimensions of the milled ridge-lap surfaces of the finished teeth "mirror" the dimensions of corresponding sockets that are milled in a denture base and receive the finished milled teeth. In a further embodiment (not shown), the new ridge-lap regions of the milled teeth may include additional retentive features in the teeth, such as "diatorics," or concave shapes in the tooth ridge-lap area to fit a corresponding convex shapes milled in the denture base. In that manner, the risk of de-bonding of the teeth from the denture base is minimized.

Figure 9:
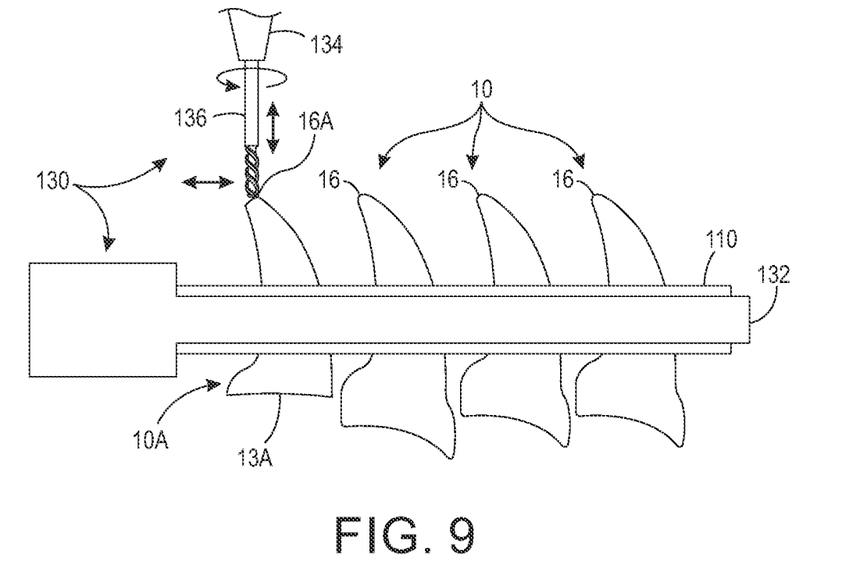
FIG. 9 is a side view of the four central incisor teeth and milling machine as shown in FIG. 7, but with the milling machine fixture having been rotated 180 degrees and the milling bur having cut some of the incisal edge of a tooth.

Referring to FIG. 9, the fixture 132 of the milling machine 130 has been rotated 180 degrees in the horizontal plane, and the milling bur 136 is shown as having cut some of the incisal edge 16A of the tooth 10A. Thus the milling machine 130 may be used to reduce the vertical dimensions of the teeth 10A and 10, and/or to define the incisal edge profiles 16A and 16 of the teeth 10A and 10, in order to improve the occlusion of the teeth, i.e., the manner in which opposing the upper or lower teeth function with the corresponding teeth 10A and 10. In the milling of posterior teeth (not shown), such as molars, the milling bur may be used to remove material from the cusps of the teeth in the same manner.

The milling of the teeth 10 continues as shown in FIGS. 8 and 9 to a completed state, in which the ridge lap surfaces are optimal for fitting to a denture base, and in which the vertical height is as desired, and in which the profile of the incisal edges is optimal for use in mastication. High quality artificial teeth are thus produced by the methods and devices disclosed herein.

It is, therefore, apparent that there has been provided, in accordance with the present invention, methods and devices for making artificial denture teeth. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

I claim:
1. A method for making artificial teeth for use in a dental prosthesis, the method comprising:
 a) inserting a plurality of artificial teeth into an elastomeric material of a nest, and contacting respective distal edges of each of the plurality of teeth with an upper planar surface of a rigid bottom of the nest that is contiguous with the elastomeric material of the nest;
 b) forming a rigid fixative contiguous with the elastomeric material of the nest, thereby embedding a central region of each of the plurality of teeth in the rigid fixative and rendering each of the plurality of teeth in a fixed position;
 c) separating the nest from the rigid fixative and from the plurality of teeth;
 d) securing the rigid fixative with the plurality of teeth in fixed positions on a milling machine; and
 e) milling at least one of the plurality of teeth to desired dimensions.

2. The method of claim 1, wherein the forming the rigid fixative is performed by applying a flowable material to the elastomeric material, the flowable material subsequently forming the rigid fixative.

3. The method of claim 1, further comprising scanning the rigid fixative with plurality of teeth in fixed positions to obtain three-dimensional data on the at least one of the plurality of teeth prior to milling the at least one of the plurality of teeth to desired dimensions.

4. The method of claim 3, wherein the three-dimensional data of the at least one of the plurality of teeth prior is used by a computer controlling the milling of the at least one of the plurality of teeth to desired dimensions.

5. The method of claim 1, wherein the fixed positions are predefined using a computer aided design software program.

6. The method of claim 1, wherein the milling of the at least one of the plurality of teeth to desired dimensions is performed by a milling machine controlled by a computer according to a CAD-CAM program.

7. The method of claim 1, wherein ridge-lap surfaces of the at least one of the plurality of teeth are milled to desired dimensions.

8. The method of claim 1, wherein the milling of the at least one of the plurality of teeth to desired dimensions includes milling retentive features in the ridge-lap surfaces of the at least one of the plurality of teeth.

9. The method of claim 1, wherein the distal edges of the at least one of the plurality of teeth are milled to desired dimensions.

10. The method of claim 1, wherein the milling of the at least one of the plurality of teeth to desired dimensions includes milling the distal edges of the at least one of the plurality of teeth to provide desired vertical dimensions of the at least one of the plurality of teeth.

11. The method of claim 1, wherein the milling of the at least one of the plurality of teeth to desired dimensions includes milling the distal edges of the at least one of the plurality of teeth to provide improved occlusion of the at least one of the plurality of teeth.

* * * * *